United States Patent [19]
Seymour et al.

[11] Patent Number: 5,510,616
[45] Date of Patent: Apr. 23, 1996

[54] CIGARETTE DENSITY PROFILE MEASUREMENT SYSTEM

[75] Inventors: Sydney K. Seymour; Bain C. McConnell, both of Clemmons; Philip A. Deal, Winston-Salem; Wayne M. Furin, Clemmons; Calvin W. Henderson, Winston-Salem; William R. Jarvis, Winston-Salem; Wallace R. Lassiter, Winston-Salem, all of N.C.

[73] Assignee: R. J. Reynolds Tobacco Company, Winston-Salem, N.C.

[21] Appl. No.: 233,157

[22] Filed: Apr. 25, 1994

[51] Int. Cl.$^6$ ................................................. G01N 23/08
[52] U.S. Cl. ........................................ 250/308; 250/360.1
[58] Field of Search ................................. 250/308, 360.1

[56] References Cited

U.S. PATENT DOCUMENTS 4,373,188  2/1983  Dowding et al. ........................ 364/522

*Primary Examiner*—Constantine Hannaher

[57] ABSTRACT

A cigarette density profile measurement system which utilizes a hopper system for storing a large number of cigarette rods whose density is to be measured which hopper system is used to feed one cigarette rod at a time to a fixed cigarette holder which incorporates a beta gauge system which sequentially irradiates a slice of the cigarette rod with beta particles for measurement of the mass of tobacco contained in that slice of the cigarette rod. By measuring the number of beta particles which pass through each slice of the cigarette rod, the cigarette density profile measurement system is able to determine the density of the tobacco contained in the cigarette rod being measured. A programmed microcomputer is utilized to control the cigarette density profile measurement system and is also provided with additional software for analyzing the density data.

17 Claims, 4 Drawing Sheets

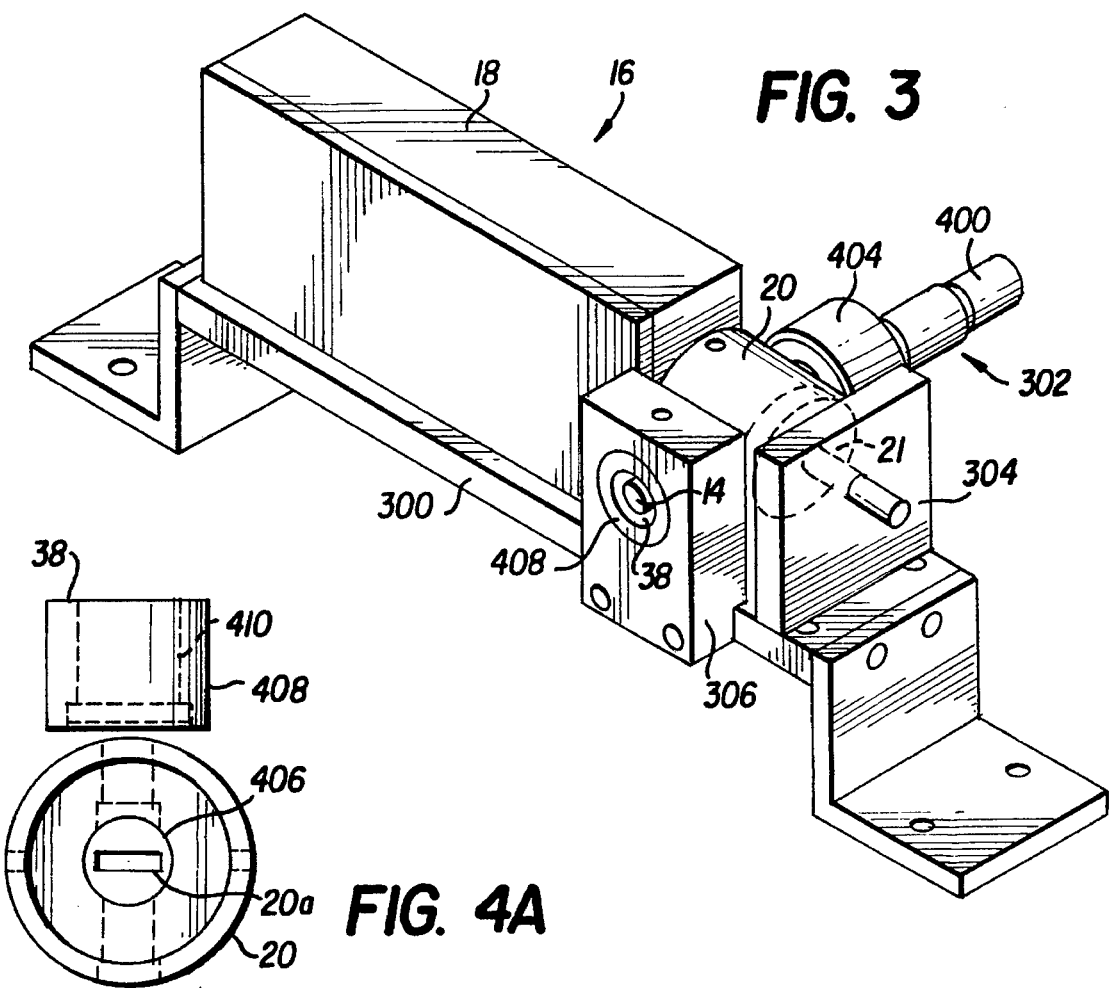
FIG. 3
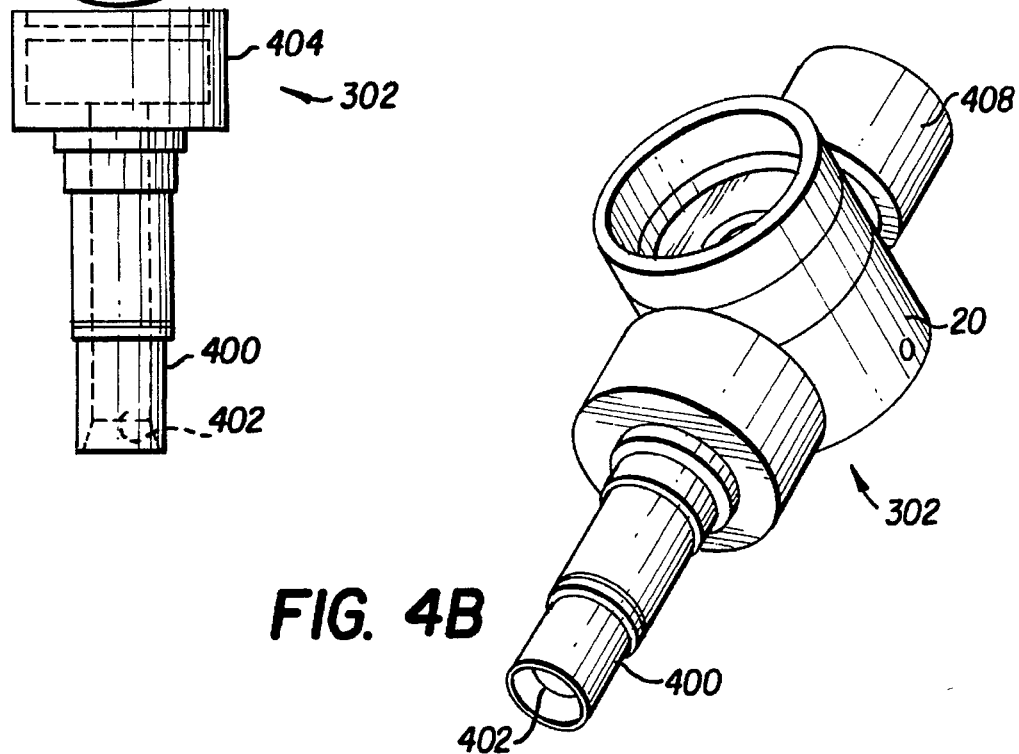
FIG. 4A
FIG. 4B

CIGARETTE DENSITY PROFILE MEASUREMENT SYSTEM

BACKGROUND OF THE INVENTION

The present invention is directed to a digital system for measuring the density of a material in a rod-shaped package. More particularly, the present invention is directed to a digital cigarette rod density measurement system for obtaining a density profile of the tobacco contained in a cigarette rod.

Manufacturers of material packaged in cylindrical packages, for example, cigarette rods containing tobacco, are interested in ascertaining whether the manufacturing process is properly manufacturing cigarettes to the design specifications. One such design specification is the percentage of tobacco and air contained within a cigarette rod.

Cigarettes are typically manufactured such that a predetermined amount of tobacco is contained within each rod. In order to determine whether the manufacturing process is operating properly, as well as to provide a tool for developing cigarette rod products which utilize more air and less tobacco in the cigarette rod, it is useful to be able to determine the weight or mass of tobacco contained within a cigarette rod.

Prior art devices for obtaining a rod density profile of a cigarette are known. One such device, however, only measures the rod density in an indirect manner using near near infrared radiation (NNIR). NNIR technology, while useful in some chemical determinations, has limitations when applied to measure the mass of tobacco in a cigarette. For example, such devices must be calibrated with dry samples in order to obtain a correlation for dry cigarette rod weight. Wet tobacco weight must be estimated after the moisture content of the tobacco is obtained by utilizing an additional method. Another significant limitation of NNIR technology is that NNIR radiation does not penetrate optically opaque material such as aluminum foil. This limitation presents a serious difficulty for known prior art devices when used with cigarette rods which incorporate a laminated aluminum foil wrap or other optically opaque materials.

The present invention, utilizes beta particles, which react directly to only the total mass of the material in their path. Such beta particles do penetrate aluminum foil. Thus, the present invention is able to account for the aluminum foil by using a weight offset. Utilizing the present invention, the greater the material present in front of the beta particles, the fewer particles that are transmitted through to a sensor on the other side of the material or cigarette rod. The remainder of the beta particles are scattered back by the material of the cigarette rod or are absorbed by that material.

The overall absorption of the beta particles has been found to follow an exponential law which can be expressed in the following equation:

$$I = I_o e^{(-1.0 \cdot u \cdot x)}$$

where $I_o$ is the number of particles detected without the material, I is the number of particles detected after passing through the material, u is the mass absorption coefficient of the material in $cm^2/g$ and x is the density thickness of the material expressed in $g/cm^2$. Using this equation, the cigarette density measurement system of the present invention can determine the mass of a slice of a cigarette by measuring the particle count both with and without the cigarette slice in the path of the emitted beta particles. The measurement using the present invention is robust and does not suffer from the blend sensitivity exhibited by prior art devices.

Another shortcoming of the known devices used to obtain rod profile measurements is that such devices typically utilize analog detectors, even in instances where a beta gauge is utilized. A digital beta detector is significantly more efficient than the analog ion chamber utilized with such prior art devices and therefore a small source of radiation is utilized. Also, the use of an analog ion chamber requires complex analog circuitry with temperature compensation in order to process the output signal. The cigarette density measurement system of the present invention, on the other hand, produces a digital output which requires only a counter for accumulating the number of beta particles to obtain a reading, thus eliminating the need for temperature compensation in order to acquire accurate data. Lastly, the known prior art devices for obtaining cigarette rod profile measurements are much more costly to produce than the present invention.

SUMMARY AND OBJECTS OF THE INVENTION

In view of the foregoing, it should be apparent that there still exists a need in the art for a cigarette rod density measurement system which is cost effective and easy to use and yet which measures cigarette rod density profiles more accurately than existing cigarette rod profile measuring systems. It is, therefore, a primary object of the present invention to provide a cigarette density measurement system which utilizes digital electronics and which produces a cigarette rod density profile with a great degree of accuracy.

More particularly, it is an object of this invention to provide digital cigarette density measurement system as aforesaid having simple and reliable electronic circuitry which does not require frequent alignment nor costly components.

Still more particularly, it is an object of this invention to provide a digital cigarette density measurement system which operates automatically to measure the density of a plurality of cigarette rods which are loaded into the hopper of the system.

Briefly described, these and other objects of the invention are accomplished by providing a cigarette hopper system which stores a large number of cigarette rods whose density is to be measured and, when commanded, feeds one cigarette at a time into a fixed cigarette holder to which a beta source and digital detector have been secured. The beta particle source is on continuously and irradiates a slice of the cigarette rod being measured with beta particles. The digital detector, under control of a microcomputer, senses the number of beta particles which pass through the tobacco in the cigarette rod being measured and impinge upon a beta particle sensor. A digital pulse is generated for each of the beta particles that exceed a threshold level which is sensed by the beta particle sensor. The cigarette rod being measured is then axially indexed to the next measurement position and another slice of the cigarette rod is irradiated with beta particles. The digital pulses generated by the sensor are counted by a digital counter board in the microcomputer and stored in the microcomputer for later retrieval and analysis. The cigarette density measurement system of the present invention is controlled and operated by software which is also stored in the microcomputer. An additional software program is utilized to analyze the data generated by the cigarette density measurement system.

BRIEF DESCRIPTION OF THE DRAWINGS

FIG. 3 is a perspective drawing of the beta gauge measurement system utilized with the cigarette density measurement system of the present invention;

FIG. 4A is a front view of the cigarette receiving element of the beta gauge system of the cigarette density measurement system of the present invention;

FIG. 4B is a perspective view of the cigarette receiving element of the beta gauge system of the cigarette density measurement system of the present invention;

DETAILED DESCRIPTION OF THE PREFERRED EMBODIMENT

Figure 1:
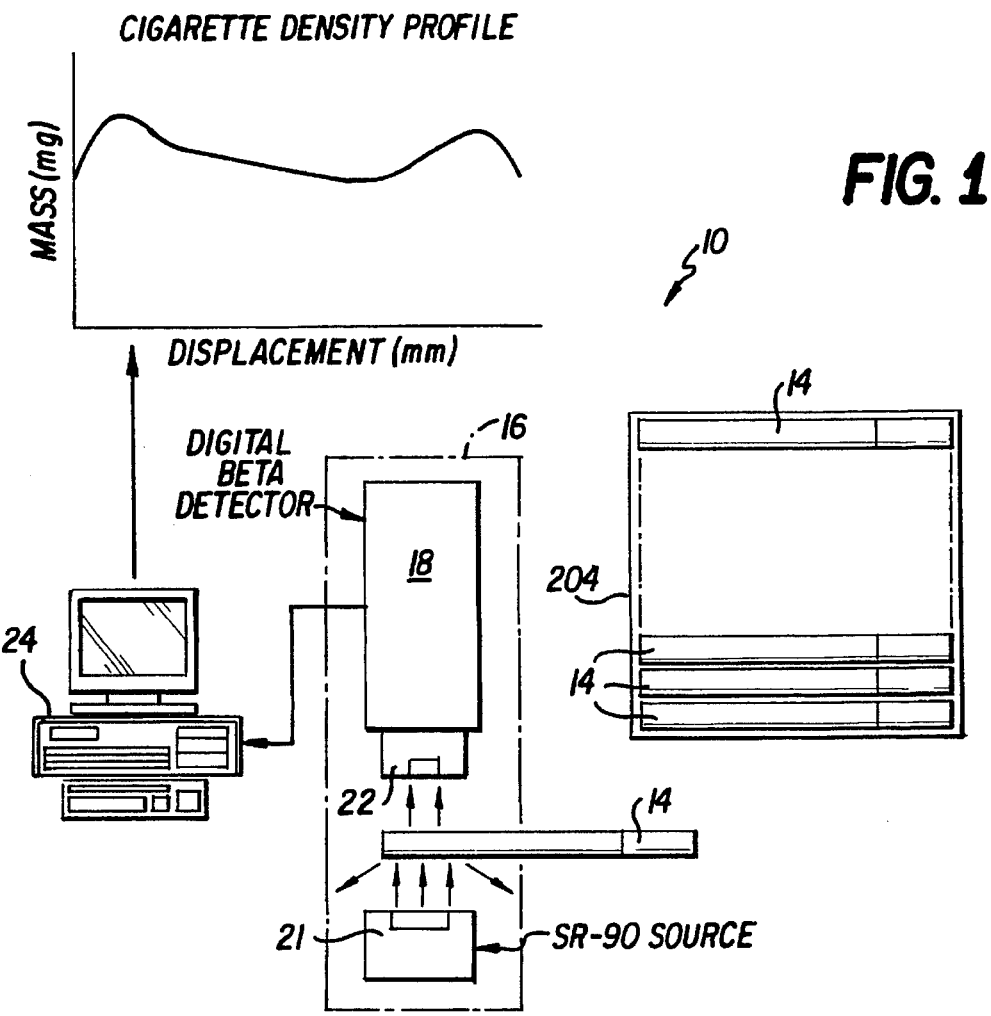
FIG. 1 is a block pictorial diagram of the cigarette density measurement system of the present invention.

Referring now in detail to the drawings wherein like elements are indicated by like reference numerals throughout, there is shown in FIG. 1 a pictorial diagrammatic representation of the cigarette density measurement system 10 of the present invention. The cigarette density measurement system 10 of the present invention is formed from four basic elements. The first element is a hopper system 204 which will be described in greater detail in connection with FIG. 2A–2B. The function of the hopper system 204 is to store a large number of cigarettes 14 whose density is to be measured and, when commanded, to feed one cigarette 14 at a time to the next element of the instant cigarette density measurement system 10.

The second element which forms part of the cigarette density measurement system 10 of the present invention is the beta gauge system 16. The beta gauge system 16 of the present invention, which is shown in more detail in FIGS. 3 and 4A–4B, is formed from a digital beta gauge 18, a source of beta radiation 21 and a beta gauge sensor 22. The source of beta radiation 21 utilizes, for example, a strontium-90 radioactive source of, for example, 500 microcuries. The cigarette rod 14 whose density is to be measured is placed between the digital beta gauge 18 and the source of beta radiation 21 by a guide block 20 in such a manner that the beta radiation source 21 emits its radiation in a direction mostly perpendicular to the length of the cigarette rod 14.

The beta radiation emitted by the beta source 21 is either absorbed by the tobacco in the cigarette 14, is back-scattered by the tobacco in the cigarette rod 14 or passes through the tobacco in the cigarette rod 14. The beta particles which pass through the cigarette rod 14 are segregated by passing through an aperture 20a in the guide block 20 approximately 2 mm wide×10 mm high and impinge upon a beta gauge sensor 22. The typical aperture size used is 10 mm×4 mm which forms pan of the digital beta detector 18. The digital beta detector 18 provides an output which indicates that a beta particle has impinged on the beta sensor 22. The beta gauge sensor 22, digital beta gauge 18 and the beta source 21 are available from ATI of Gaithersburg, Md. as Model No. AT100.

The third component of the instant cigarette density measurement system 10 is a personal computer 24 which may be of the IBM AT class or compatible or a more powerful IBM or compatible personal computer. The personal computer 24 is connected directly to the digital beta gauge 18 to receive its output. A counter board (not shown) is utilized in the personal computer 24 to count each of the particles detected by the beta sensor 22 as represented by a pulse generated by the digital beta gauge or detector 18. By accumulating the number of detected beta particles and computing either or all three of the absorbance, the percent absorbed or transmittance (percentage), the cigarette density measurement system 10 of the present invention is able to generate the cigarette density profile shown, for example, in FIG. 1.

Figure 5:
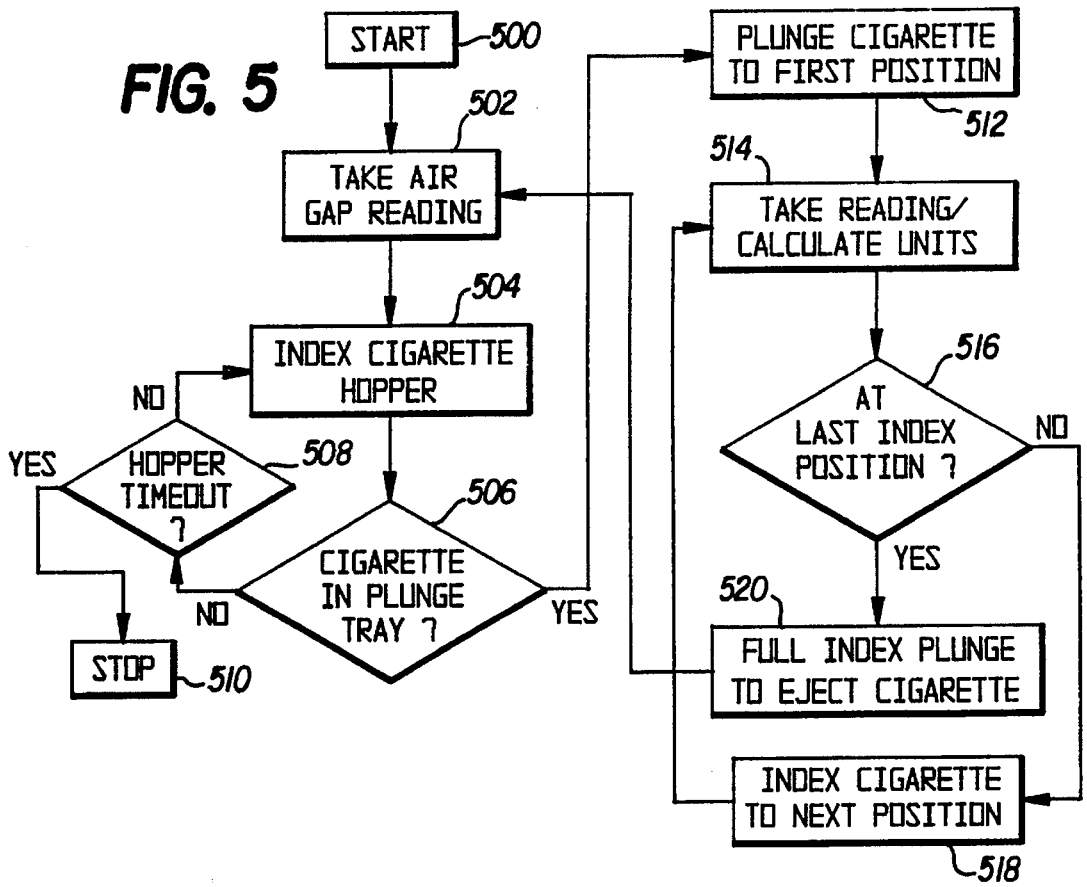
FIG. 5 is a diagram of the flow chart of the software used for operating the cigarette hopper system and beta gauge system of the cigarette density measurement system of the present invention.
Figure 6:
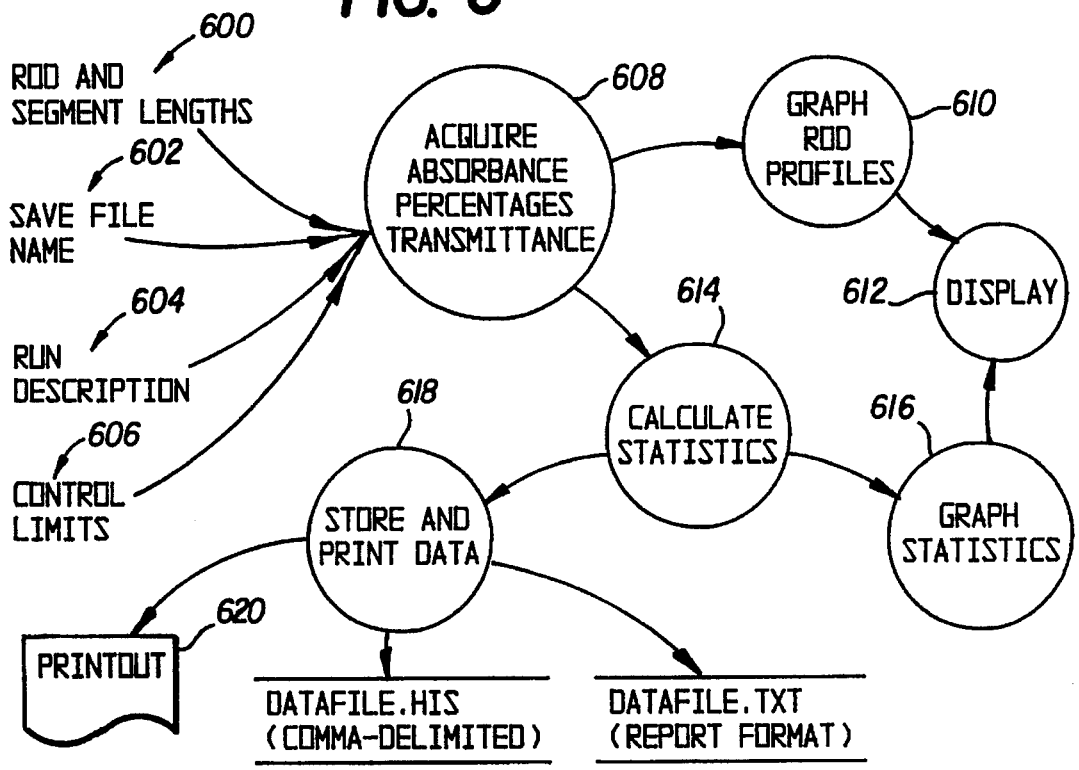
FIG. 6 is a data flow chart diagram of the software which operates on the computer system component of the cigarette density measuring system of the present invention to analyze the data generated by the beta gauge system of the present invention.

The fourth element of the instant cigarette density measurement system 10 is the software components shown in diagrammatic flowchart form in FIGS. 5 and 6. The operating software represented by the flowchart shown in FIG. 5 is utilized to operate the hopper system 204 and the beta gauge system 16. The digital beta gauge 18 produces a signal indicative of each receipt of a beta particle having passed through the cigarette rod 14 being sampled and impinging on the beta detector 22. The operating software shown in flowchart form in FIG. 5 operates on the personal computer 24.

The diagram of the software data flow shown in FIG. 6 illustrates the data flow software which also operates on the personal computer 24. Such data flow software is used to process the data obtained by the cigarette density measurement system of the present invention under operation by the density measurement or operating software.

Figure 2B:
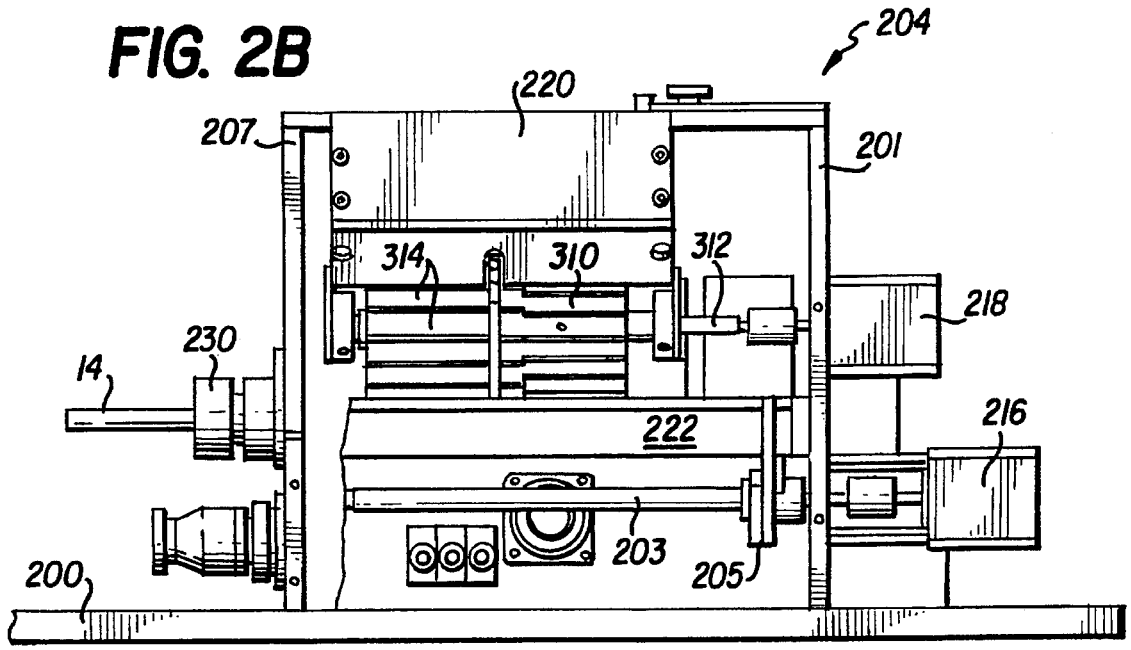
FIG. 2B is a side elevation drawing of the hopper system of FIG. 2A.
Figure 2A:
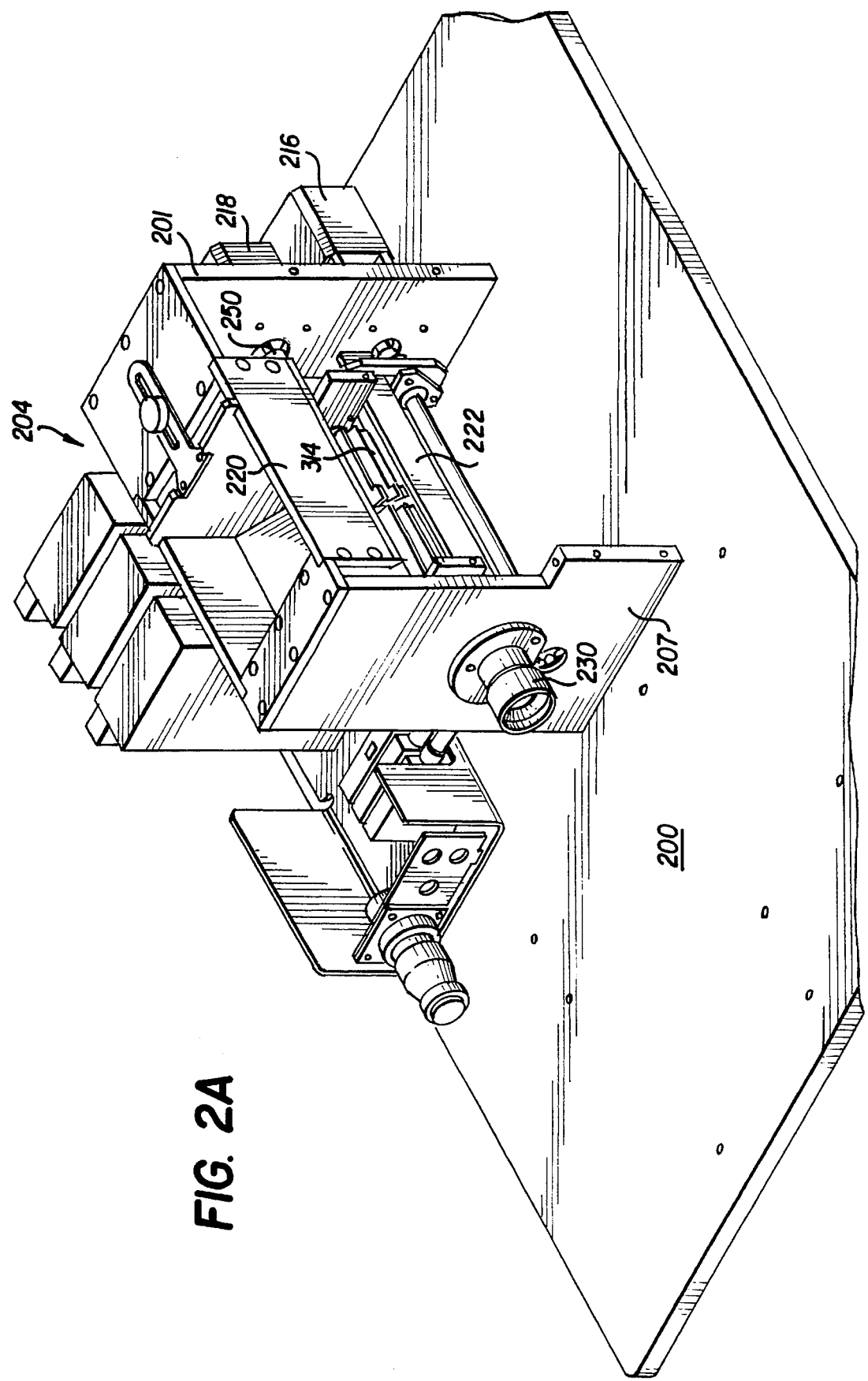
FIG. 2A is a perspective drawing of the hopper system utilized with the cigarette density measurement system of the present invention.

FIGS. 2A and 2B show the mechanical system of the present invention for storing and handling a number of cigarettes in a hopper system or assembly 204 and for presenting a single cigarette 14 at a time to the cigarette receiving element 400. The cigarette storage assembly of the present invention is assembled on a base 200 made from any suitable rigid material, such as aluminum sheet plate. The hopper assembly 204 is secured to the base 200 by suitable means and is used to store the quantity of cigarette samples which is to be measured by the instant invention. Typically, a batch of about 50 sample cigarette rods is loaded into the hopper assembly 204, and subjected one at a time to the beta particles from the beta source 20, although batches of any number of samples could be used.

The hopper assembly 204 includes a motor 218 which is mounted to an end plate 201 of the hopper assembly 204 and drives the hopper drum 310 by means of a suitable connector, such as a drive shaft 250. The hopper drum 310 is constructed with a plurality of fins 314 extending around the circumference of the drum 310. Each of the fins 314 is spaced from the next adjacent fin by a distance sufficient to allow a cigarette to easily rest therebetween.

The hopper drum 310 is situated within the hopper assembly 204 directly beneath the cigarette hopper 220. The cigarette hopper 220 is first filled with cigarettes to be measured. The hopper drum 310 is then indexed or rotated a predetermined amount, under control of the microcomputer 24. That allows a cigarette 14 to drop between each pair of fins 314 such that, as the drum 310 continues to rotate when indexed, one cigarette 14 is dropped into a channel 222 which extends below the hopper drum 310 and across the entire length of the hopper assembly 204 along an axis parallel to the axis of rotation of the hopper drum 310.

A plunger motor 216 is mounted to end plate 201 of the hopper assembly 204 and is also operated under control of the microcomputer 24. When so instructed, the motor 216 rotates a threaded shaft 203 which serves to advance a plunger 205 from right to left as viewed in FIG. 2B. The plunger 205 pushes a cigarette 14 which has been dropped by the hopper drum 310 into the channel 222 along the length of the channel 222 until the tobacco rod portion of the cigarette 14 exits at the opposite end of the channel 222 through a cigarette holder 230.

The cigarette holder 230 may be formed from any suitable construction such that it is able to hold a cigarette 14 in a position approximately parallel to the base 200. One such construction comprises a plurality of flexible fingers extending radially inwardly from an annular ring or sleeve such that the filter portion is gripped by the fingers. About 70 mm of a typical 100 mm filter cigarette preferably protrudes from the cigarette holder 230 into the cigarette receiving element 400.

The cigarette holder 230 is mounted to the end plate 207 of the hopper assembly 204 and is aligned with the cigarette channel 222 such that the cigarette to be measured 14 travels smoothly through the cigarette channel 222 when pushed by the plunger 205 operated by the plunger motor 216 and exits from the end of the cigarette holder 230 for measurement by the digital beta gauge system 18.

The bracket 300 of the digital beta gauge 18 is securely mounted to the base 200 in such a position that the entire portion of the cigarette rod 14 which protrudes from the cigarette holder 230 extends into the cigarette receiving element 400. In order to accomplish that, the cigarette receiving element 400 is positioned in close proximity to the cigarette holder 230.

In operation, the hopper 220 is first loaded with approximately 50 cigarettes whose density or mass is to be measured. The hopper drum 310 is then rotated/indexed by the motor 218 under a command from the microcomputer 24 such that a single sample cigarette is selected by means of the multiple vanes 314 arranged around the circumference of the hopper drum 310. In that manner, a single cigarette is dropped into the cigarette channel 222 where it is pushed, by means of a plunger 205 operated by the motor 216 down the length of the channel 222 until it exits from the cigarette holder 302 and protrudes into the cigarette receiving element 400 such that approximately 70 percent of the length of the cigarette is contained inside of the cigarette receiving element 400 to be subjected to beta particle radiation from the beta particle source 21. Each succeeding cigarette, as it is loaded into the cigarette holder 230, pushes out the cigarette 14 then held by the cigarette holder 230. Each cigarette 14 is pushed through the length of the cigarette receiving element 400 and exits from the opposite end of the cigarette holder 302, as is described later.

Under control of the microcomputer 24 and its associated software, the beta source 21 irradiates a slice of the cigarette rod 14, for example, 2 mm wide as provided by the apperture 20a. The beta particles which reach the beta sensor 22 are detected and digital pulses are transmitted by the digital beta gauge 18 to the microcomputer 24 for counting. After the slice of the cigarette rod 14 has been irradiated with beta particles, the motor 216 is utilized to index the cigarette rod 14 another 2 mm past the beta source 21 and window 20a for irradiation. The process is repeated as many times as necessary in order to scan the complete length of the cigarette 14, or for as many segments as are programmed in the computer 24 to produce the desired density profile. The stored measurements for each of the segments of the sample cigarette being measured are then plotted sequentially on the computer screen/or stored in the hard disk of the computer 24 in order to obtain results for the entire sample. The next cigarette is then selected from the hopper 220 and the process described above begins again for that new sample. The system of the present invention continues to measure each of the cigarettes placed in the hopper 220 until the hopper is empty, at which time the system enters a stand-by mode.

FIG. 3 is a perspective view of the beta gauge system 16 of the present invention shown mounted on a U-shaped bracket 300 which is used to mount the beta gauge system 16 to the base 200 to which the hopper system 204 is also mounted. The height of the U-shaped bracket 300 is designed such that the hopper system 204 inserts a cigarette rod 14 directly into the guide block 20.

A second cigarette holder 302 is secured to both the end plate 207 and to the guide block 20. A second bracket 306 is attached to the U-shaped bracket 300. The support 306 includes a hole 38 through which the cigarette rod 14 is ejected from the guide block 20 after it has been subjected to the beta particles for the purpose of calculating its density or mass.

The second cigarette holder 302 is shown in more detail in FIGS. 4A and 4B. The cigarette holder 302 is formed from a hollow cigarette receiving element 400 having a tapered inlet. The inside diameter of the cylindrical cigarette receiving element 400 of the cigarette holder 302 is of a uniform diameter of a size slightly larger than the diameter of the cigarette rods 14 which are to be measured. The hollow inside portion of the cigarette receiving element 400 forms a rod measurement channel 402.

The cigarette receiving element 400 of the cigarette holder 302 is connected to a second cigarette receiving element 404 which is of larger outside and inside diameter than the cylindrical element 400 and which connects both the cigarette receiving element 400 and the cigarette measurement channel 402 to the guide block 20 which includes the aperture 20a in the collimator 406 through which the beta particles pass after passing through the cigarette rod 14. The final element of the cigarette holder 302 is a third cylindrical element 408 which is connected to the opposite end of the guide block 20 than the second cylindrical element 404 and which is of smaller outside and inside diameter than the second cylindrical element 404. The third cylindrical element 408 has an inside diameter of about at least two times the diameter of the cigarette measurement channel 402 and forms an ejection channel 38. The third cylindrical element 408 is mounted within the support bracket 306.

FIG. 5 is a diagram of a flow chart of the software which is used to operate the cigarette density measurement system 10 of the present invention. As previously described, the software depicted in FIG. 5 operates on the personal or microcomputer 24. Once the software is started at step 500, an air gap reading is taken at step 502. The purpose of the air gap reading is to serve as the reference value for $I_o$. This also adjusts for any changes which occur in the source/ detector systems between measurements of different cigarettes. Then, the cigarette hopper system 204 is given an instruction to move to its next index position, thereby allowing a cigarette rod to be placed into the channel or plunge tray 222. At step 506, a determination is then made as to whether a cigarette rod 14 is present in the plunge tray 222. If it is determined at step 506 that there is no cigarette present in the plunge tray 222, then a determination is made at step 508 of whether the hopper time out period has expired. If an affirmative determination is made at step 510 meaning that the hopper system 204 is empty, then the measurement flow software program stops.

If a negative determination is made at step 508, meaning that more cigarettes 14 remain in the hopper system 204 for measurement, then the cigarette hopper 310 is indexed at step 504 and a determination is then made again at step 506 of whether there is a cigarette rod 14 present in the plunge tray 222.

If an affirmative determination is made at step 506 that a cigarette 14 is present in the plunge tray 222 then the cigarette is plunged to its first position at step 512. That means that the plunger 205 of the cigarette hopper system 204 pushes the cigarette into position such that the cigarette holder 230 is holding the filter of the cigarette rod 14 and the cigarette rod 14 is in the measurement channel 402 with the end of the cigarette rod 14 opposite the filter in a position in front of the apperture 20a. The beta gauge 18 is then turned on at step 514 and the digital signal output by the digital beta gauge 18 is received and counted by the counter board for a predetermined period of time (preferably 200 msec) and the result is stored in the appropriate file in the personal computer 24.

A determination is then made at step 516 of whether the cigarette rod 14 is at its last index position. If a negative determination is made at step 516, then the hopper system 204 is instructed to index the cigarette rod 14 to its next position and then step 514 is repeated again. If it is determined at step 516 that the cigarette rod 14 is in its last index position, then the cigarette rod 14 being measured is ejected by the plunger and exits the cigarette holder 302 through the ejection channel 410 and the opening 38. The software then causes an air gap reading to be taken at step 502, causes the cigarette hopper 204 to index the next cigarette at step 504, determines whether a cigarette rod is in the plunge tray 222 at step 506 and then continues on as described previously.

As discussed above, the cigarette rod 14 is indexed 2 mm at a time until the entire length of the cigarette rod has been subjected to the beta particle source 21. The cigarette density measurement system 10 continues to operate automatically as described above until all of the cigarettes contained in the hopper 220 of the cigarette hopper system 204 have been measured. At that time, the measurement flow software stops at step 510.

FIG. 6 is a data flow diagram of the density profile software which is used to make certain calculations as well as to calculate statistics and print and store data for later use. Data from the measurement flow software, the flowchart of which is depicted in FIG. 5, is acquired by the density profiler software, as rod and segment lengths 600. The file name 602 as well as the run description 604 and the control limit 606 are all inputted into the density profiler software which then determines the beta particle absorbance percentages at step 608. Using that data, the density profiler software then graphs the rod profiles such as that shown in FIG. 1 at step 610. Such rod profiles can then be displayed at step 612, either using the monitor connected to the personal computer 24 or by using a printer (not shown) connected to the personal computer 24.

In addition, after step 608, various statistics, such as the Absorbance (Absorbance= 20 Ln $I_o/I$), the $$\text{Percent Absorbed} = \left[ \frac{I_o - I}{I_o} \right] \times 100$$

by each cigarette rod and the segment of each rod as well as the average, standard, minimum and maximum absorbance percentage for each segment of all of the rods can then be calculated at step 614, graphed at step 616 and displayed at step 612. Alternatively, the statistics calculated at step 614 can be stored in various data files or printed out at step 618, such as by using a paper print out at step 620. In that manner, the mass of a slice of each cigarette rod in each of its 2 mm segments can be determined and displayed for comparison.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. A system for measuring the density profile of each of a plurality of cigarette rods, comprising:

a hopper system for storing a plurality of cigarette rods to be measured and for feeding said plurality of cigarette rods one at a time;

a cigarette receiving element located adjacent to said hopper system for receiving each one of said plurality of cigarette rods;

a digital beta gauge system for irradiating each one of said plurality of cigarette rods with beta particles and for producing an output signal for each beta particle which passes through each one of said plurality of cigarette rods; and a digital data processor for receiving the output signals from said digital beta gauge system and for generating a density profile measurement for each one of said plurality of cigarette rods measured by said measuring system.

2. The system of claim 1, wherein said hopper system, under control of said digital data processor, feeds an individual cigarette rod from said hopper system into said cigarette receiving element.

3. The system of claim 1, wherein said hopper system includes a plunger for indexing each one of said plurality of cigarette rods fed to said cigarette receiving element through a predetermined number of positions such that at least one portion of each one of said plurality of cigarette rods is irradiated by said beta particles.

4. The system of claim 1, wherein one of a predetermined number of slices of said one of said plurality of cigarette rods being irradiated is irradiated at a time under control of said digital data processor.

5. The system of claim 4, wherein said digital data processor calculates a density profile measurement for each one of said plurality of cigarette rods by summing said received output signals from said beta gauge system for each of said predetermined number of slices of each one of said plurality of cigarette rods.

6. The system of claim 1, wherein said digital beta gauge includes a source of beta particles of 500 microcuries in strength.

7. A method for measuring the density profile of a material contained in a rod-shaped package, comprising the steps of:

storing a plurality of said rod-shaped packages in a container;

providing a package receiving element for holding each one of said plurality of said rod-shaped packages during the measuring of the density profile of the material contained in said rod-shaped package;

moving each one of said plurality of rod-shaped packages into said package receiving element, one at a time;

irradiating each one of said plurality of rod-shaped packages with beta particles when one of said plurality of rod-shaped packages is in said package receiving element;

generating a series of digital signals corresponding to numbers of beta particles which penetrate through said material contained in each one of said plurality of rod-shaped packages during said irradiating step; and receiving said series of digital signals and producing a density profile measurement of said material contained in each one of said plurality of rod-shaped packages.

8. The method of claim 7, further including the step of indexing each one of said plurality of rod-shaped packages through a predetermined number of positions and irradiating said material contained in said rod-shaped package with beta particles such that at least one portion of said material in said rod-shaped package is substantially irradiated by said beta particles.

9. The method of claim 8, wherein each of said irradiations at each of said predetermined number of indexed positions irradiates a slice of said material with beta particles.

10. The method of claim 9, wherein said step of receiving said series of digital signals includes the step of summing said series of digital signals associated with each slice of material in order to obtain a density profile measurement of said at least one portion of said material contained in said rod-shaped package.

11. The method of claim 7, further including the step of ejecting each one of said rod-shaped packages from said package receiving element after it has been substantially irradiated along its length by beta particles.

12. A method for measuring the density profile of a material contained in a rod-shaped package under control of a digital data processor, comprising the steps of:

storing a plurality of said rod-shaped packages in a container system;

providing a package receiving element for sequentially receiving each one of said plurality of said rod-shaped packages from said container system;

commanding said container system to feed one of said plurality of said rod-shaped packages from said container system into said package receiving element;

subjecting said one of said plurality of said rod-shaped packages fed into said package receiving element to irradiation by beta particles, under control of said digital data processor;

generating a plurality of digital signals corresponding to received beta particles passing through said material of said rod-shaped package being irradiated by said beta particles; and transmitting said plurality of digital signals to said digital data processor for producing a density profile measurement of said material in said rod-shaped package irradiated by said beta particles.

13. The method of claim 12, further including the step of indexing, under control of said digital data processor, said one of said plurality of rod-shaped packages fed into said package receiving element.

14. The method of claim 13, wherein said step of indexing causes said one of said plurality of rod-shaped packages to be irradiated along its length by said beta particles such that a slice of said material is made at each indexing position.

15. The method of claim 14, wherein said density profile measurement of said material is produced by said digital data processor in part by adding each of the plurality of digital signals of said slices obtained at each indexing position.

16. The method of claim 12, further including the step of ejecting said rod-shaped package contained in said package receiving element after said irradiating step is completed.

17. The method of claim 16, wherein said step of ejecting is controlled by said digital data processor.

\* \* \* \* \*